US012295666B2

(12) United States Patent
Jacobsen et al.

(10) Patent No.: US 12,295,666 B2
(45) Date of Patent: May 13, 2025

(54) ELECTROMAGNETIC DISTORTION CORRECTIONS FOR KNOWN DISTORTERS

(71) Applicant: Medtronic Navigation, Inc., Louisville, CO (US)

(72) Inventors: Bradley W. Jacobsen, Erie, CO (US);
Victor D. Snyder, Erie, CO (US);
Robert Pahl, Broomfield, CO (US);
Andrew J. Wald, Denver, CO (US);
Steven Hartmann, Superior, CO (US);
Dominic M. Graziani, Louisville, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 698 days.

(21) Appl. No.: 17/454,921

(22) Filed: Nov. 15, 2021

(65) Prior Publication Data

US 2022/0183764 A1    Jun. 16, 2022

Related U.S. Application Data

(60) Provisional application No. 63/125,874, filed on Dec. 15, 2020.

(51) Int. Cl.
*A61B 34/20*     (2016.01)
*A61B 34/30*     (2016.01)
*G01R 29/08*     (2006.01)

(52) U.S. Cl.
CPC ............. *A61B 34/20* (2016.02); *A61B 34/30* (2016.02); *G01R 29/0814* (2013.01); *A61B 2034/2051* (2016.02); *A61B 2034/2055* (2016.02)

(58) Field of Classification Search
CPC ............ A61B 34/20; A61B 2034/2051; A61B 2017/00725; A61B 2034/2055
See application file for complete search history.

(56) References Cited

U.S. PATENT DOCUMENTS 6,073,043 A * 6/2000 Schneider ................ A61B 5/06
324/207.11
8,131,342 B2   3/2012 Anderson
(Continued)

OTHER PUBLICATIONS

International Preliminary Report on Patentability, corresponding to PCT/US2021/072879, Date of Issuance of Report: Jun. 13, 2023.

*Primary Examiner* — Jermele M Hollington
*Assistant Examiner* — Temilade S Rhodes-Vivour
(74) *Attorney, Agent, or Firm* — Harness, Dickey & Pierce, P.L.C.

(57) ABSTRACT

Systems and methods for correcting experienced EM fields measured at each of one or more EM trackers of an EM tracking system as such measurements are influenced by a known distorter are disclosed herein. An EM emitter may transmit an EM field such that it contains the one or more EM trackers. The system then determines a pose of a distorter within the EM field. The system receives, from each EM tracker, data representing experienced EM fields as distorted by a distortion field caused by the distorter. The system proceeds to determine the distortion field using the pose and a model comprising one or more characteristics of the distorter. The system may first optimize the model. The system calculates data representing corresponding corrected experienced EM fields based on each respective experienced EM field and the determined distortion field at the same location.

21 Claims, 9 Drawing Sheets

(56) References Cited

U.S. PATENT DOCUMENTS

| | | |
|---|---|---|
| 9,522,045 B2 | 12/2016 | Ramachandran |
| 9,710,836 B1* | 7/2017 | O'Malley ............ G06Q 30/0607 |
| 9,733,336 B2 | 8/2017 | Shen et al. |
| 2003/0016006 A1* | 1/2003 | Khalfin .................. A61B 5/062 |
| | | 324/207.17 |
| 2003/0184285 A1* | 10/2003 | Anderson .............. A61B 34/20 |
| | | 606/1 |
| 2005/0107687 A1 | 5/2005 | Anderson |
| 2006/0055712 A1 | 3/2006 | Anderson |
| 2007/0078334 A1* | 4/2007 | Scully ...................... A61B 5/06 |
| | | 600/424 |
| 2007/0225594 A1* | 9/2007 | Anderson .............. A61B 90/36 |
| | | 600/424 |
| 2007/0244666 A1* | 10/2007 | Li .......................... G01B 7/003 |
| | | 702/94 |
| 2008/0161684 A1* | 7/2008 | Li ............................ A61B 6/12 |
| | | 600/417 |
| 2008/0174303 A1* | 7/2008 | Anderson ............... G01D 5/208 |
| | | 324/207.17 |
| 2014/0354300 A1 | 12/2014 | Ramachandran et al. |
| 2017/0258529 A1 | 9/2017 | Winne |
| 2019/0242952 A1 | 8/2019 | Schneider |
| 2019/0380791 A1 | 12/2019 | Fuerst et al. |

\* cited by examiner

ELECTROMAGNETIC DISTORTION CORRECTIONS FOR KNOWN DISTORTERS

RELATED APPLICATIONS

This application claims priority to U.S. Provisional Application No. 63/125,874 filed on Dec. 15, 2020 and titled "Electromagnetic Distortion Correction for Known Distorters" which is hereby incorporated by reference in its entirety.

TECHNICAL FIELD

The present disclosure relates generally to devices and systems used to track objects. For example, embodiments of the present disclosure involve an electromagnetic (EM) system used to track the pose (e.g., a position and an orientation) of anatomical structures and/or surgical tools during corrective surgery.

DETAILED DESCRIPTION

Figure 1:
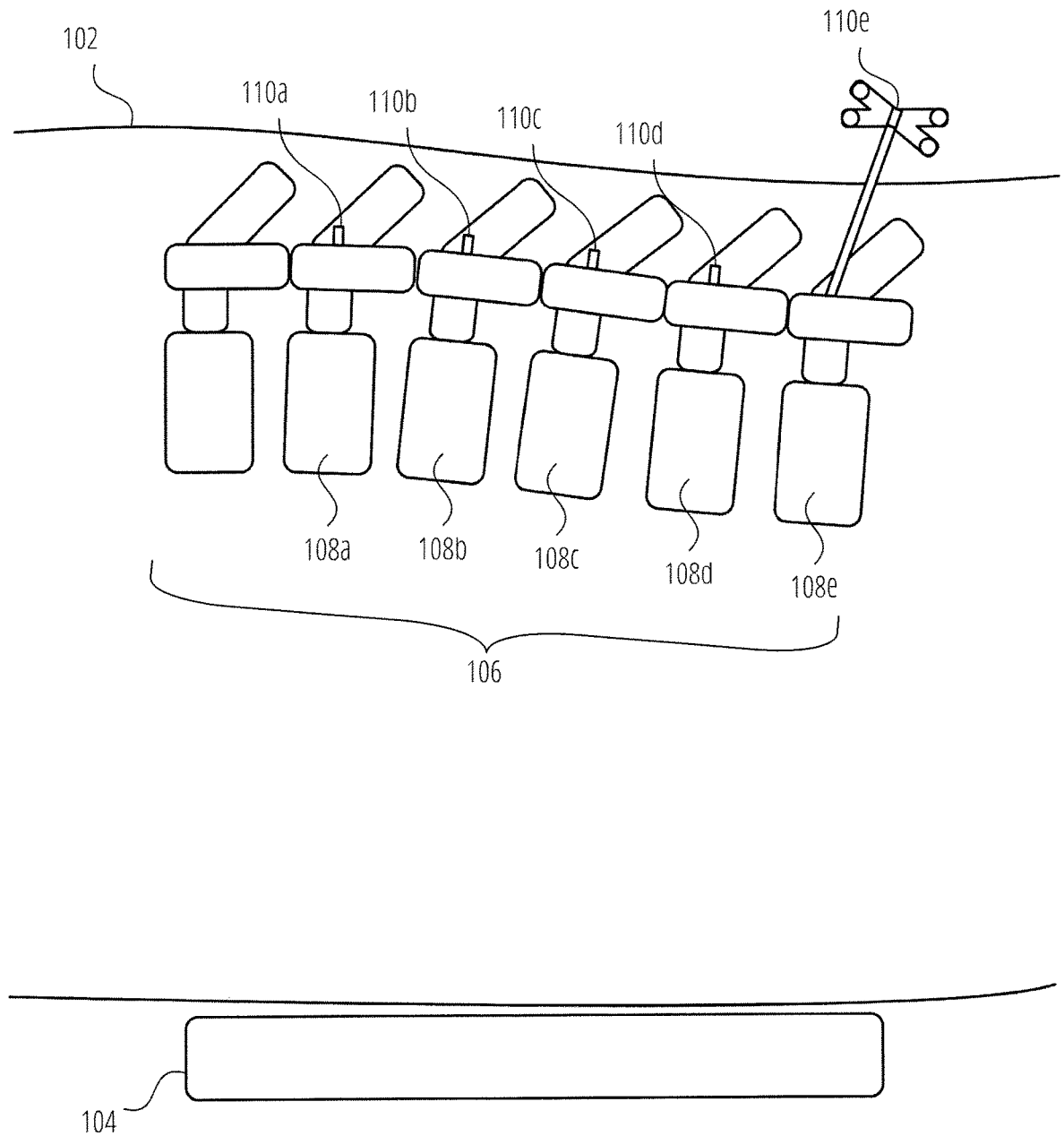
FIG. 1 illustrates the use of an EM tracking system with a patient, according to an embodiment.

Electromagnetic (EM) tracking systems may be used during a surgical procedure for tracking one or more anatomical structures that are being or may be moved (or for which pose information, including position and/or orientation, is otherwise relevant) during the surgical procedure. EM tracking systems can also track one or more surgical tools during the surgical procedure. For example, an EM emitter transmits, emits, or generates one or more EM fields with one or more known characteristics. One or more EM trackers attached to one or more of the anatomical structures and/or surgical tools measure and report their individually experienced EM fields back to the EM tracking system. By analyzing the data so generated, the pose(s) (e.g., positions(s) and orientation(s)) of the one or more anatomical structures or surgical tools may be determined.

In certain instances, for example, a corrective surgery may be performed on a patient to treat or correct an acute injury, a chronic injury, or a chronic disease (e.g., scoliosis) related to one or more anatomical structures (e.g., spinal vertebrae) of the patient. For example, a corrective spinal surgical procedure may be performed to align displaced or misaligned vertebrae while retention implants or hardware is secured to the vertebrae. An EM tracking system may be used during the procedure to track a pose of a vertebra relative to an adjacent vertebra to facilitate determining the degree of displacement and/or the degree of alignment of the vertebrae. It is anticipated that other items could also be tracked using EM trackers. Such EM tracking may occur within a spatial volume defined by and for use with the EM tracking system.

One or more EM trackers are each attached (or coupled) to an anatomical structure of the patient. The EM trackers detect field strengths, directions, and/or components of the EM field(s) received at their positions using one or more sensors (this disclosure describes the detected nature of a transmitted EM field acting on an EM tracker as an "experienced EM field" of the EM tracker). EM trackers may also be capable of generating one or more EM fields in some embodiments, which may be received by, for example, other EM tracker(s) and/or an EM receiver within the system. An EM receiver may have similar detection capabilities as an EM tracker, but may be a device within the EM tracking system that is not itself to be tracked (and in some cases may act as a known reference point within the spatial volume covered by the EM tracking system). Data is transmitted from EM trackers and/or any EM receiver to, for example, one or more processors of the EM tracking system. The processor processes the data to determine a pose of each of the EM trackers relative to adjacent EM trackers. In some embodiments, the pose of an EM tracker may be determined with reference to six degrees of freedom (including three position degrees of freedom and three orientation degrees of freedom). Using the pose of the EM tracker, the system may derive the pose of an object to which the EM tracker is attached (e.g., the pose of an anatomical structure or a tool to which the EM tracker is attached).

In some embodiments, one or more transmitted EM fields detected at the EM trackers may be generated by an EM emitter that is separate from the EM trackers, such that the poses of the EM trackers can be determined with respect to the EM emitter. Alternatively (or additionally), one or more transmitted EM fields detected at any one of the EM trackers may be generated by another of the EM trackers, such that the poses of the EM trackers can be determined with respect to each other. Alternatively (or additionally), an EM receiver that is separate from the EM trackers may receive one or more transmitted EM fields from the one or more EM trackers, such that the poses of the EM trackers can be determined with respect to the EM receiver.

In some situations when using an EM tracking system as described, a distorter is introduced into a transmitted EM field. The distorter can be, for example, a surgical tool (or part of a surgical tool) to be used during a surgical procedure during which the EM tracking system is being used. Due to interactions between the transmitted EM field and the distorter, a nonnegligible distortion field is present within the EM field and near the EM trackers, with the result that the EM field as reported by the EM trackers (and/or any EM receiver) is distorted by the distortion field. The distortion field can vary based on the distorter's pose, magnetic permeability, its electrical conductivity, its size, and/or one or more of its physical dimensions (and/or combinations of these). Experienced EM fields detected by EM trackers and/or EM receivers within the EM field may be different from an experienced EM field that would be detected by the same EM tracker without the influence of this distortion field.

The effects of such distortion fields may reduce accuracy in certain EM tracking systems that do not account for or compensate for the effects of these distortion fields (e.g., which make tracking determinations without modification to account for the effects of the distortion field on one or more EM trackers reporting the data used by the EM tracking system to make the described tracking determinations).

Embodiments herein describe methods, apparatuses, and systems for addressing the effects of these distortion fields. A distortion field generated by an interaction between a distorter and a transmitted EM field has aspects of: location, orientation, magnitude, and phase based on various properties of the distorter. For example, a pose (e.g., a position and orientation) of the distorter within the transmitted EM field and/or material characteristics of the distorter (such as shape, dimension, magnetic permeability and/or electrical conductivity) will determine the nature of the distortion field. Through measurements and/or modeling techniques described herein, these characteristics of such distortion fields can be determined or approximated. Accordingly, by using the characteristics of a distortion field affecting one or more EM trackers, embodiments herein may correct the experienced EM fields reported by the one or more EM trackers. The one or more processors of the EM tracking system may perform these tasks in order to correct the experienced EM fields that are reported by the one or more EM trackers. The one or more processors may then use the corrected experienced EM field data to generate more accurate poses of the one or more EM trackers.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

FIG. 1 illustrates the use of an EM tracking system with a patient 102, according to an embodiment. The patient 102 is disposed near an EM emitter 104. The patient 102 may be, for example, within a surgical apparatus arranged such that, among other things, a portion of interest for a medical procedure to be performed on the patient 102 is proximate to the EM emitter 104. In these cases, at least the portion of interest is within range of one or more EM fields to be transmitted by the EM emitter 104. In the example of FIG. 1, the portion of interest for the medical procedure includes a portion of the spinal column 106 of the patient 102, corresponding to a medical procedure to be performed specifically on that portion of the spinal column 106. It is contemplated that in other embodiments, other portions of interest (corresponding to other medical procedures) may be used with embodiments disclosed herein. The portion of interest may include one or more anatomical structures that are to be tracked by the EM tracking system. In the example of FIG. 1 the anatomical structures to be tracked may be the vertebrae 108a-108e of the spinal column 106.

In order to enable such tracking via an EM tracking system, one or more EM trackers may be attached to each anatomical structure that is to be tracked. In the example of FIG. 1, EM trackers 110a-110e have been attached or otherwise coupled to corresponding ones of the vertebrae 108a-108e. The interaction between an EM field transmitted by the EM emitter 104 and each of the EM trackers 110a-110e is respectively measured by the EM trackers 110a-110e and provided to the EM tracking system as experienced EM field information. This data allows the EM tracking system to track the vertebrae 108a-108e, in the manner described above.

It is contemplated that any of the EM trackers 110a-110e may serve additional purposes beyond EM tracking. For example, as illustrated, the EM trackers 110a-110d are located entirely within the patient 102. However, the EM tracker 110e extends externally from the patient 102. This may allow the EM tracker 110e to act as an optical tracker for use with an optical tracking system (which may be part of the EM tracking system) as well as an EM tracker for the EM tracking system.

Figure 2:
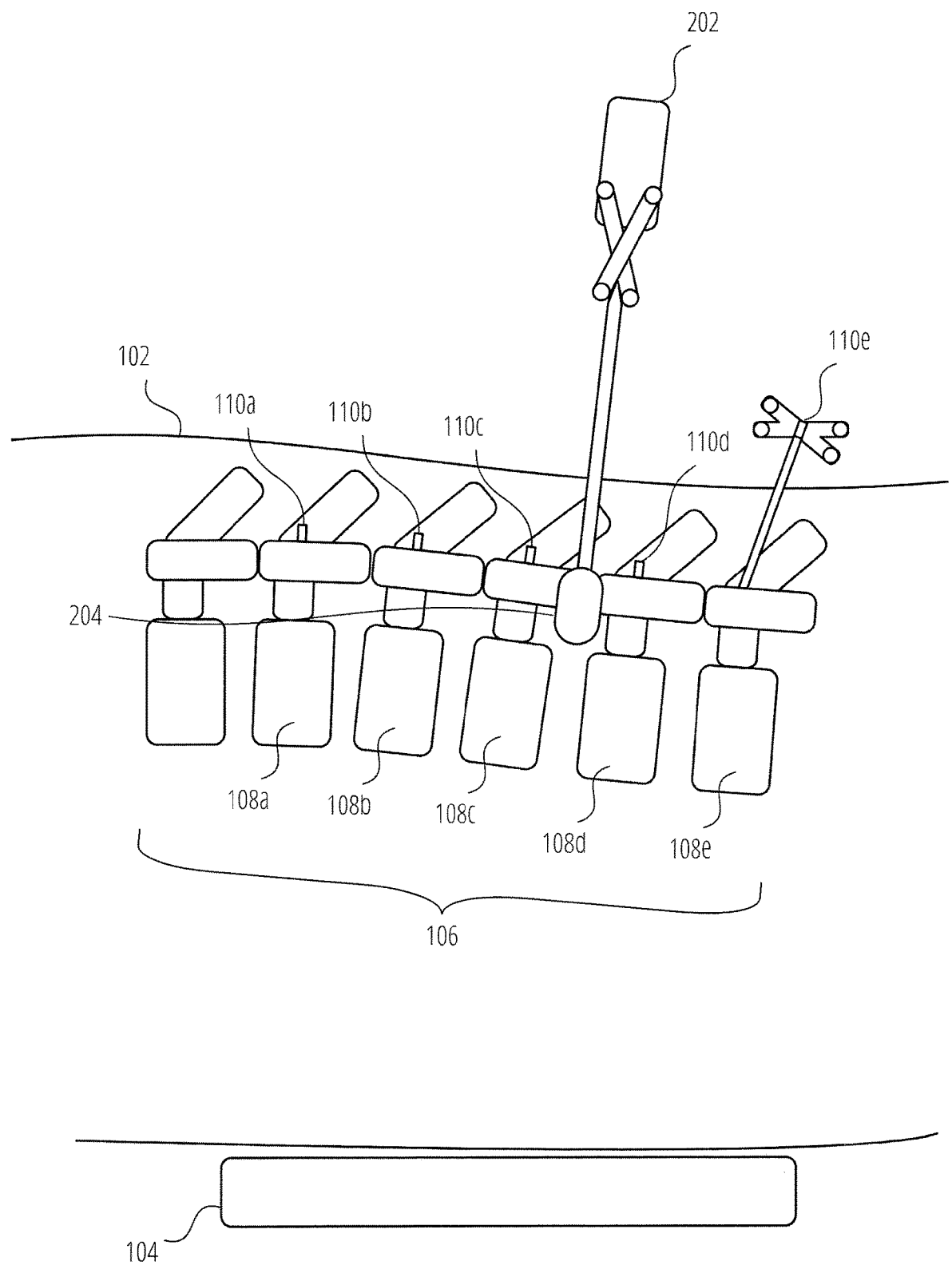
FIG. 2 illustrates the disposition of a tool near a spinal column of a patient incident to the performance of a surgical procedure, according to an embodiment.

FIG. 2 illustrates the disposition of a tool 202 near the spinal column 106 of the patient 102 incident to the performance of a surgical procedure, according to an embodiment. The tool 202 may need to be disposed near the EM trackers 110a-110e (e.g., as illustrated) in order to be used to perform a part of the surgical procedure that uses the tool 202. In the example of FIG. 2, the tip 204 of the tool 202 may have properties such that the tip 204 (either alone or as part of the tool 202) acts as a distorter. In other words, the interaction between an EM field transmitted by the EM emitter 104 and the tip 204 when the tool 202 is disposed at the illustrated pose may cause a distortion field at/around the position of the tip 204. In many cases, proximity of this (or any other) distortion field to any of the EM trackers 110a-110e may interfere with an experienced EM field measurement by the one or more of the EM trackers 110a-110e, in the manner described herein.

A distorter (such as the tip 204 or other portions of the tool 202) may be said to have a pose (including, for example, a position and an orientation) and characteristics (e.g., dimension, shape, magnetic permeability, and/or electrical conductivity, etc.) that are deterministic of certain properties (e.g., the location, orientation, magnitude, and phase) of a corresponding distortion field. An EM tracking system according to embodiments herein leverages knowledge of the pose and characteristics of the distorter (whether measured or modeled) in order to estimate or approximate the properties (e.g., the location, orientation, magnitude, and phase) of a corresponding distortion field. As will be seen, the pose of the distorter may be derived by the EM tracking system from the pose of a tool including the distorter, where it is the tool (and not just the distorter) that is being tracked by the EM tracking system. As will be described in further detail below, characteristics of the distorter (perhaps as represented relative to an entire tool that includes the distorter) may be known in one way or another prior to the surgical procedure, and thus known to the EM tracking system during the surgical procedure.

The pose of the distorter (e.g., the tip 204) may include a position of the distorter within a transmitted EM field and an orientation of the distorter relative to one or both of the EM emitter 104 and/or one or more EM trackers 110a-110e. As part of the pose, the position of the distorter may be understood to be the position of the distorter within the EM field relative to a known point in the EM field. The known point in the EM field may be, for example, a point on the EM emitter 104. As part of the positioning, the orientation of the distorter may be understood to be the orientation of the distorter relative to one or more of the EM emitter 104 and/or one or more of the EM trackers 110a-110e.

The positioning and orientation elements of the pose of the distorter may be known to/determined by the EM tracking system in various ways. For example, the pose of the distorter within the EM field may be known to the system. In some cases, it may be that the distorter is in a pre-determined pose within the EM field (and therefore at a known position within the EM field) and does not move during the surgical procedure. In other cases not involving an ability to use such posing pre-determinations (e.g., involving distorters that may be re-posed during the course of a surgical procedure, such as the tip 204 of the tool 202), the EM tracking system may track the pose of the distorter. This may be done in various ways.

For example, it may be that the distorter is physically coupled or attached to a robotic posing system (e.g., a robotic system meant to establish a position and/or orientation of objects during the surgical procedure (such as the tool 202) that either are or include the distorter). The robotic posing system may track its own configuration as part of its processes and report this configuration to the EM tracking system, which allows the EM tracking system to determine the pose (e.g., the position and/or orientation) of the distorter. For example, in the case of the tool 202, the robotic posing system may report data regarding its own configuration, from which the EM tracking system can determine a pose of the tip 204 of the tool 202 based on known physical attributes of the tool 202.

In some cases, it may (alternatively or additionally) be that the distorter is tracked using an optical tracking system (e.g., an optical system meant to optically determine a pose during the surgical procedure of one or more objects (such as the tool 202) that are or include the distorter). The optical tracking system may track and report the pose (e.g., as a position and/or an orientation) of these object(s), which allows the EM tracking system to determine the pose of the distorter. For example, in the case of the tool 202, the optical tracking system may report data regarding the pose of the tool 202, from which the EM tracking system can determine a pose of the tip 204 of the tool 202 based on known physical attributes of the tool 202.

In some cases, it may (alternatively or additionally) be that the distorter is tracked within the EM tracking system using an EM tracker on the tool 202. For example, the tip 204 of the tool 202 may be a distorter, as described, while the rest of the tool 202 does not act as a distorter. In these cases, the pose (e.g., the position and/or orientation) of the tip 204 may be tracked using an EM tracker that is attached to a portion of the tool 202 that does not exhibit a distortive effect within an EM field (and is far enough removed from the tip 204 that distortions from the tip 204 are negligible). This EM tracker may report data regarding its interaction with a transmitted EM field from the EM emitter to the EM tracking system that is used to determine the pose of said EM tracker, from which the pose of the tool 202 (and thus the position of the tip 204 of the tool 202) may be derived.

Other types of tracking are contemplated. For example, a visible light tracking system that can identify a distorter and/or a tool including the distorter (e.g., using region-based convolutional neural networks trained using machine learning methods) may be used to determine the pose of the distorter and/or a tool including the distorter. As another example, a lidar tracking system can be used to determine the pose of the distorter and/or a tool including the distorter.

It is further contemplated that multiple of these described tracking methods may be used together. When multiple of these methods are so used, the spatial volumes each uses may be co-registered such that data from one such system can inform another such system. This spatial volume may be co-registered to the spatial volume used by the EM tracking system for purposes of tracking one or more EM trackers. For example, an optical tracking system may co-register to the spatial volume used by the EM tracking system (e.g., as established relative to the use of the EM emitter and any EM trackers of the EM tracking system) for EM tracking, such that optical data from the optical tracking system may be used relative to the EM tracking methods for the EM emitter of the tool 202 (as described above) within that tracking volume. Further, a robotic posing system may (also) co-register to the spatial volume used by the EM tracking system for EM tracking, such that configuration data from the robotic posing system may be used relative to the EM tracking methods for the EM emitter of the tool 202 within that tracking volume.

The location of the distortion field may be based on the pose of the distorter. For example, in methods to be discussed, it may be that the distortion field is approximated about a point that represents the pose of the distorter.

Any characteristics of the distorter (e.g., dimension, shape, magnetic permeability, and/or electrical conductivity, etc.) may be provided to or otherwise known to the system. As will be further described below, these characteristic properties may exist as part of a general model corresponding to any given distorter and/or tool of a certain type, or as part of a specific model that is specific to a specific instance of that distorter and/or tool type.

The pose of the distorter (e.g., the position of the distorter and the orientation of the distorter) within a transmitted EM field may be deterministic of a corresponding distortion field.

The elements of the pose (e.g., the position and/or the orientation) of the distorter may be deterministic of the magnitude of the distortion field at its various points. For example, the distortion field may be approximated about a point that represents the position of the distorter. The position of the distorter then affects the magnitude of the distortion field at the various points within the distortion field, in that, for a same point within the distortion field (relative to the approximated location of the distorter), the magnitude may vary (e.g., decrease or increase) as the distorter moves relative to an EM emitter (e.g., modifies its position relative to the EM emitter). As another example, a magnitude of distortion field in a first direction may change as the orientation of a non-uniform distorter changes (as the locations of the non-uniformities relative to the first direction changes). Such non-uniformities may be in distorter shape, distorter material, etc. The relationship between the elements of the pose (e.g., the position and/or the orientation) of the disorder relative to the EM emitter and the magnitude of the various points making up the distortion field corresponding to the distorter may be known to (via experimentation) or modeled by (using the physical attributes of the distorter) the EM tracking system.

The pose of the distorter may be deterministic of the orientation of the distortion field. As the distorter moves from a first pose to a second pose within an EM field, the direction of the EM field relative to the distorter may be different at the new location. Accordingly, the corresponding distortion field may have a different direction at the second location than the corresponding distortion field at the first location.

The characteristics of the distorter (e.g., dimension, shape, magnetic permeability, and/or electrical conductivity) within a transmitted EM field may be deterministic of a corresponding distortion field.

The dimensions of the distorter may be deterministic of the magnitude, at various points, of the distortion field caused by the distorter. For example, distorters of one dimension may cause distortion fields to have magnitudes at various points that are different than distortions of analogous points when using distorters of a second dimension. The relationship between a dimension of a distorter and the magnitude of one or more points of the distortion field due to that dimension may be known to (via experimentation) or modeled by (based on the known dimension) the EM tracking system.

The shape of the distorter may be deterministic of the magnitude, at various points, of the distortion field. For example, the relative magnitude of the distortion field for various points that are equidistant from the approximated-about point of the distorter in various directions may roughly track the shape of the distorter. The relationship between a shape of a distorter and the magnitude of various points of the distortion field in various directions due to that shape may be known to (via experimentation) or modeled by (based on the known shape) the EM tracking system.

The magnetic permeability of the distorter may be deterministic of the magnitude and phase of the distortion field.

For example, the magnitude at various points of the distortion field caused by the distorter may generally increase as the magnetic permeability of the distorter increases. The relationship between a magnetic permeability of a distorter and the magnitude of the various points of the distortion field due to that magnetic permeability may be known to (via experimentation) or modeled by (based on mathematical estimations and/or experimentations on other distorters) the EM tracking system.

As another example, the phase of the distortion field may vary away from zero (relative to an EM emitter) in the case that the magnetic permeability of the distorter is nonlinear. For example, for nonlinear magnetic materials with nonnegligible coercivities and losses, the magnetic phase may shift from the phase of the EM emitter by some amount $\varepsilon$. This magnetic phase shift may be expressed via a complex magnetic permeability.

The electrical conductivity of the distorter may be deterministic of the magnitude and phase of the distortion field.

For example, distorters with higher electrical conductivities may generate distortion fields that are greater in magnitude at various points within the distortion field than a distorter with a lower electrical conductivity. The relationship between an electrical conductivity of a distorter and the magnitude of the distortion field due to that electrical conductivity may be known to (via experimentation) or modeled by (based on mathematical estimations and/or experimentations on other distorters) in the EM tracking system.

As another example, the phase of the distortion field for a conductive distorter may start out at $=\pi/2$ (relative to the phase of the EM emitter). However, given the distorter pose, geometry, and materials, this $\pi/2$ value may further shift by some $\Delta$, where $\Delta$ depends largely on effective inductance and resistance of the distorter.

Note that given a conductive and magnetic distorter, aspects of both magnetic permeability and electrical conductivity arise and interact. For example, a distorter's magnetic permeability increases its effective inductance via magnetic flux concentration and its resistance via the induced current skin depth.

It should be understood that 1) elements of the pose (e.g., position and orientation) and/or 2) various characteristics (dimension, shape, magnetic permeability, and/or electrical conductivity) of a distorter may jointly together be deterministic of the nature of the distortion field. This means that multiple (including all) of these factors may be simultaneously used within the system to determine an appropriate model for a distortion field corresponding to the distorter, using the relevant principles discussed above related to each such factor.

Figure 3:
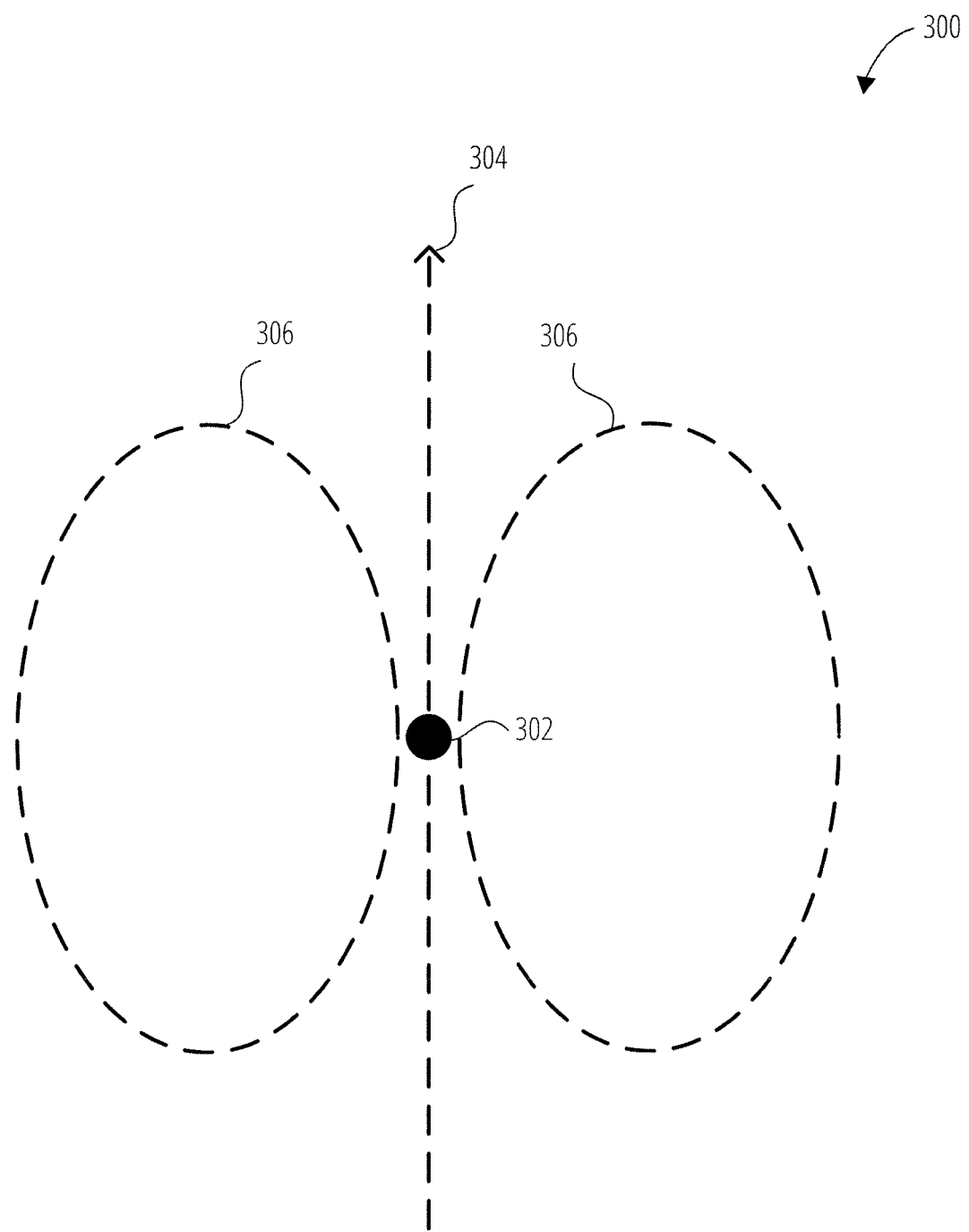
FIG. 3 illustrates a dipole model, according to an embodiment.

FIG. 3 illustrates a dipole model 300, according to an embodiment. The dipole model 300 may be used to conceptually represent a distortion field according to embodiments disclosed herein. While in the illustrated embodiment a dipole model 300 is used, in some embodiments, the distortion field may be modeled as one of a multiple dipole, a multipole, an effective charge, an effective current, a boundary element method model, a finite element analysis model, a measurement-based model or any other numerical approximation of the distortion field.

The dipole model 300 may include a center 302. The center 302 may represent the location of a distortion field caused by a distorter, as described above.

The dipole model 300 may also include an orientation 304, which may correspond to the direction of the EM field relative to the pose of the distorter for which the corresponding distortion field is being approximated by the dipole model 300. The orientation 304 of the dipole model 300 may impute directional meaning to the distortion field lines 306 of the dipole model 300 representing the distortion field. The distortion field lines 306 represent a portion of the magnetic field caused by the interaction between a transmitted EM field and the distorter. Note that one or more distortion field lines may be modeled within EM tracking systems described herein with much higher fidelity than is apparent in the dipole model 300 as illustrated in FIG. 3 (which is presented in a schematic form).

While presented here visually, it is anticipated that a dipole model 300 representing a distortion field (and its various parts, such as the center 302, the orientation 304, and the distortion field lines 306) may be calculated and/or stored in the systems herein described in a parameterized fashion (e.g., the dipole model 300 may not necessarily need to be explicitly "drawn" in order to perform methods described herein).

It is contemplated that other model types could be used to model distortion fields. For example, a distortion field could be represented using a multiple dipole model, a multipole model, a line, or a surface model such as an effective charge or current model, or an otherwise parameterized model such as a boundary element method or a measured and interpolated model. In these cases, the EM tracking system may include a lookup table (e.g., in a memory) that can be used in combination with current distorter pose information to determine a distortion field as a model of, e.g., distorter geometry, distorter conductivity, and/or distorter magnetic permeability.

Further, it is also contemplated that such a model could be built by finite element modeling and/or direct measurement. In these cases, the EM tracking system may then include in a memory a lookup table that can be used to determine a distortion field as a model of, e.g., distorter pose, distorter geometry, distorter conductivity, and/or distorter magnetic permeability.

While the use of a different model to represent a distortion field may cause a different result from the dipole case, the principles behind the use of distortion fields as so modeled would remain analogous to the methods described in the dipole case used by example herein.

Figure 4:
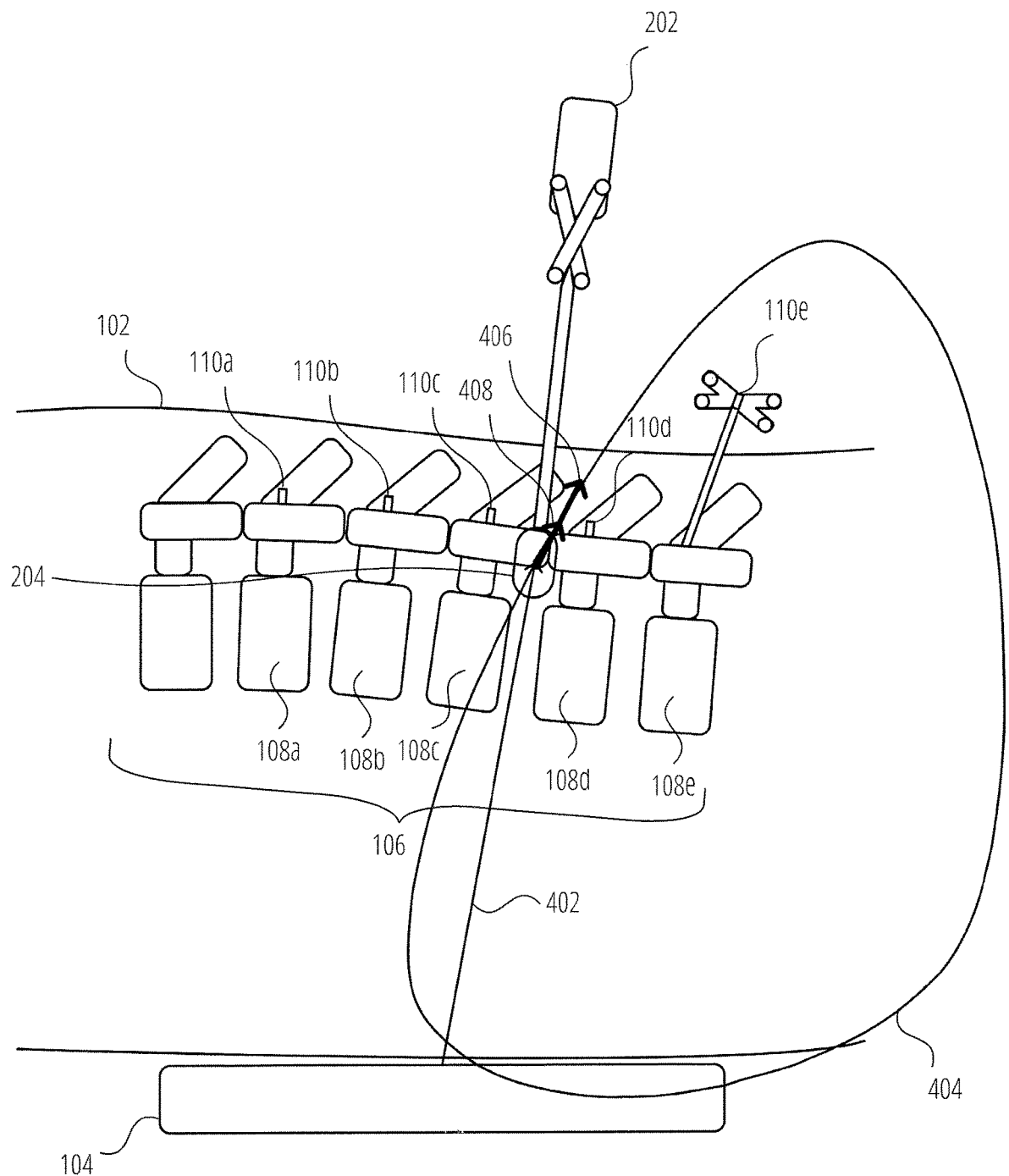
FIG. 4 illustrates the disposition of the tool near a spinal column of a patient incident to the performance of a surgical procedure, when an EM emitter is transmitting an EM field, according to an embodiment.

FIG. 4 illustrates the disposition of the tool 202 near the spinal column 106 of the patient 102 incident to the performance of a surgical procedure, when the EM emitter 104 is transmitting an EM field, according to an embodiment. The elements of FIG. 4 may be used to initialize an approximation (e.g., using a dipole model) of the distortion field generated by the interaction of the EM field with the tip 204 of the tool 202. The center 402 of the tip 204 of the tool 202 may be a vector measured relative to, for example, the center of the EM emitter 104 using methods of, for example, an optical tracking system, a robotic posing system, and/or an EM tracker of the tool 202 for determining distorter poses, as described above.

The magnetic field portion of the EM field transmitted by the EM emitter 104 (referred to herein as B) may be represented (at least in part) by one or more magnetic field lines. One of these magnetic field lines is the magnetic field line 404, which illustrates the direction of B at each point on the magnetic field line 404, consistent with the magnetic field vector 406, which represents both the magnitude and the direction of B at the illustrated point (the center 402 of the tip 204).

An initial distorter magnetic moment 408 (referred to herein as $M_i$) for the tip 204 may be determined relative to the magnetic field vector 406 at the position of the tip 204 of the tool 202. The initial distorter magnetic moment 408 may be calculated by:

$$M_i = B \, f_i(\mu_r, \sigma, \text{geometry}), \text{ where}$$

$\mu_r$ is the (relative) magnetic permeability of the distorter; $\sigma$ is the electrical conductivity of the distorter; and $f_i$ is a function corresponding to the geometry of the distorter.

For example, for a distorter that is approximately spherical, taking $\sigma \approx 0$ and $\mu_r > 1$, $f_i$ is equal to $(4\pi a^3/\mu_0)((\mu_r-1)/(\mu_r+2))$.

An initial distorter phase (referred to herein as $4\delta\phi_i$) may be calculated by:

$$\delta\phi_i = g_i(\mu_r, \sigma, \text{geometry}), \text{ where}$$

$\mu_r$ is the (relative) magnetic permeability of the distorter; $\sigma$ is the electrical conductivity of the distorter; and $g_i$ is a function corresponding to the geometry of the distorter.

For example taking $\sigma = 0$ and $\mu_r > 1$ and $\mu_r \in \mathbb{R}$, $g_i$ is equal to 0.

Once $M_i$ is known, an initial distortion field (which may be referred to herein as $D_i$) may be determined with $D_i(M_i, r)$. Accordingly, $D_i$ may be said to be an approximation of the distortion field caused by the distorter. In one example, where the initial distortion field is modeled using a dipole, the relevant calculation/expression may be $$D_i(M_i, r) = \mu_0(3(M_i \bullet e_r)e_r - M_i)/(4\pi r^3), \text{ where}$$

r is the vector from the dipole center to the position of interest within the approximated distortion field, and $e_r$ is the unit vector along r.

Figure 5:
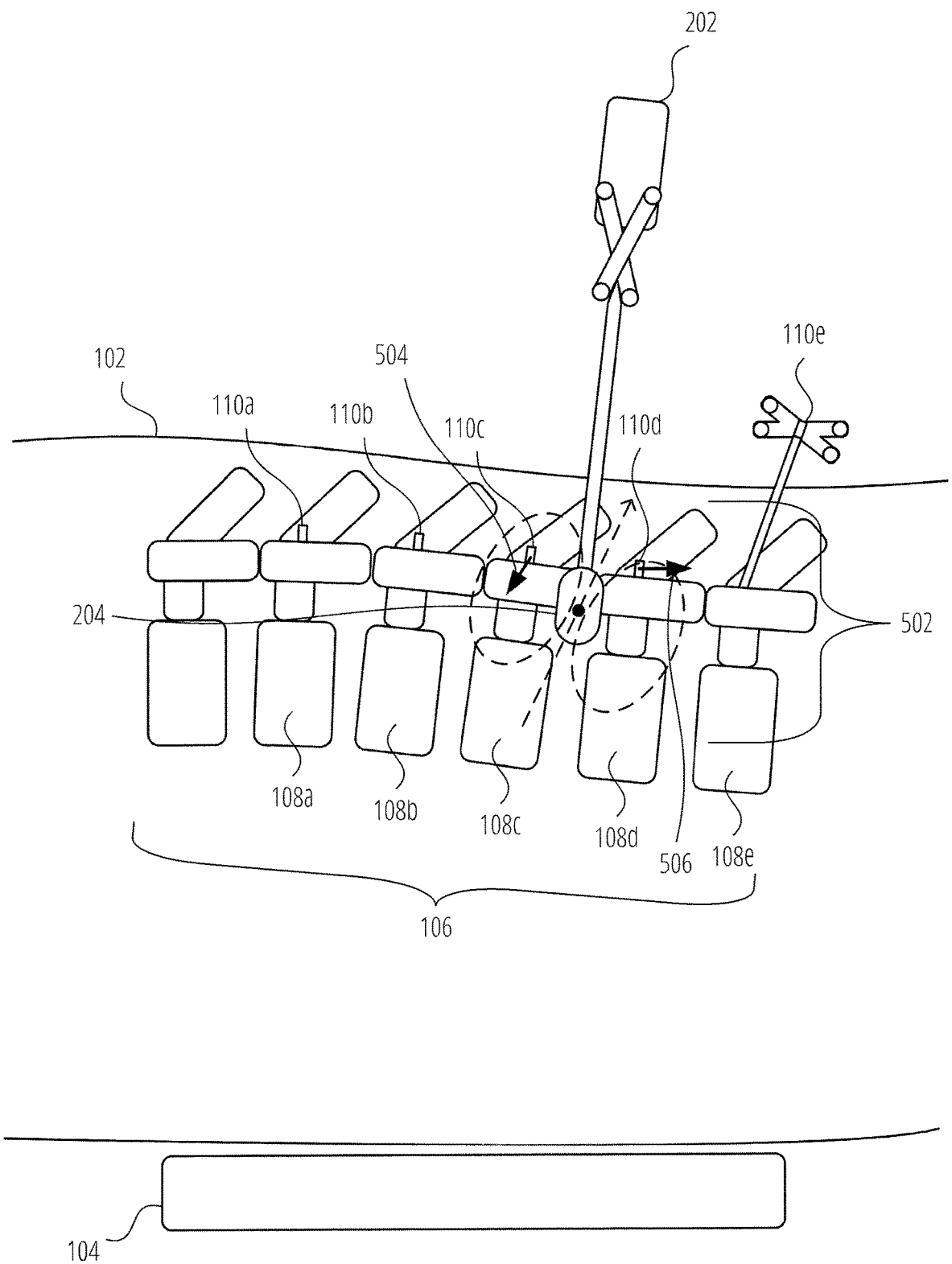
FIG. 5 illustrates the disposition of a tool near a spinal column of the patient incident to the performance of a surgical procedure, with an initial distortion field superimposed over a tip of the tool, according to an embodiment.

FIG. 5 illustrates the disposition of the tool 202 near the spinal column 106 of the patient 102 incident to the performance of a surgical procedure, with an initial distortion field 502 superimposed over the tip 204 of the tool 202, according to an embodiment. The tip 204 of the tool 202 acts as a distorter corresponding to the initial distortion field 502. The initial distortion field 502 may conceptually represent $D_i$ (when using a dipole model).

As illustrated, the EM tracker 110c and the EM tracker 110d are near the tip 204. Accordingly, the system presumes some non-zero distortive effect on these EM trackers based on the initial distortion field 502.

Because the pose of the tip 204 of the tool 202 is known (e.g., via a robotic posing system, an optical tracking system, and/or an EM tracker of the tool 202, using methods described above) relative to positions of each of the EM tracker 110c and the EM tracker 110d (information that may be determined using the known position of the tip 204 and position data for the EM tracker 110c and the EM tracker 110d from prior to the introduction of the tool 202 into the patient 102), a first distortion vector 504 and a second distortion vector 506 may be determined using $D_i(M_i, r)$, in the manner described above. Accordingly, a first distortion vector 504 (corresponding to the position of the EM tracker 110c) and a second distortion vector 506 (corresponding to the position of the EM tracker 110d) may represent the presumed effect of the initial distortion field 502 at the positions of the first distortion vector 504 and the second distortion vector 506 and may be calculated accordingly.

It is contemplated that in some embodiments, the pose of and/or one or more characteristics of the distorter (and/or a tool including the distorter) may be optimized or refined prior to their use in determining a distortion field approximation for use in the system. This optimized pose and/or characteristics may be used in order to create an optimized distortion field $D_o$. In these embodiments, it may then be that $D_o$, rather than any $D_i$, is used to calculate one or more distortion vectors.

For example, it may be that the memory of an EM tracking system contains a general model for the distorter and/or the tool including the distorter that comprises one or more characteristics (e.g., geometry, magnetic permeability, electrical conductivity, etc.). This general model may be based on what is pre-presumed (e.g., a pre-programmed parameterization) about the distorter and/or the tool including the distorter. It may alternatively be that this general model is based on prior experience by the EM tracking system with a distorter and/or a tool including the distorter that is the same type as the current distorter and/or tool including the distorter. For example, the EM tracking system may include a general model of the tool 202 and/or its tip 204. In some cases, the characteristics from a general model for a distorter and/or a tool including the distorter are used to calculate $D_i$ in the manner described above.

The general model for the distorter may have been pre-stored within the memory of the EM tracking system.

Alternatively (or additionally), it is contemplated that the EM tracking system may receive the general model for the distorter and/or the tool including the distorter from a memory that is found on the distorter and/or the tool including the distorter, and/or by receiving an identifier from the distorter and/or the tool including the distorter (e.g., a radio frequency identification (RFID) from the distorter and/or the tool including the distorter) and using this identifier to locate a general model for the distorter and/or the tool including the distorter from a server accessible over a network on which the EM tracking system communicates.

It may be noticed/understood that, due to manufacturing variances (or other reasons), the distorter and/or a tool including the distorter may not exactly match the general model corresponding to the distorter and/or a tool including the distorter. For example, a magnetic permeability of the tip 204 of the tool 202 may be slightly different than expected, based on slight material variations. As another example, a size of the tool 202 may be slightly different than the general model corresponding to the tool 202. Accordingly, it may be that the system is capable of using collected data (e.g., experienced EM field data) by one or more EM trackers taken while under the influence of a distortion field caused by the distorter to extrapolate relevant differences between the characteristics of the distorter and/or tool including the distorter (e.g., dimension, shape, magnetic permeability, and/or electrical conductivity, etc.) as recorded in the general model and the actual characteristics of the specific physical instance of distorter and/or the tool including the distorter based on these measured responses.

Such differences may be determined by comparing the experienced EM field data to predicted experienced EM field data that is determined by using the current pose of the distorter and/or tool including the distorter with the characteristics of the general model (e.g., according to the initial distortion field $D_i$, in the manner described above). Based on the delta between the experienced EM field data and the predicted experienced EM field data, differences between characteristics recorded in the general model and characteristics of the actual distorter and/or tool including the distorter can be extrapolated. These characteristic differences may then be applied to the general model corresponding to the distorter and/or the tool including the distorter, resulting in a specific model for the specific distorter and/or tool including the specific distorter.

The collected data (e.g., pose data and experienced EM field data) used for model optimization purposes is not necessarily any data that was collected uniquely for the purpose of this optimization. For example, such collected data so used may in some cases be prior pose data and corresponding EM response data generated when the distorter (and/or the tool including the distorter) was in a prior pose within the EM field for other purposes.

Further, it is also contemplated that a (previously optimized) specific model could be even further optimized by (repeating) an analogous process for the distorter and/or tool including the distorter as those described above for optimizing the general model. Accordingly, it is anticipated that the characteristics of a specific model for a distorter and/or a tool including the distorter may become more and more accurate the more the distorter and/or a tool including the distorter is used within the system for various purposes.

The specific model for the distorter may then be stored within the memory of the EM tracking system. Alternatively (or additionally), it is contemplated that the EM tracking system may store the specific model for the distorter and/or the tool including the distorter to a memory that is found on the distorter and/or the tool including the distorter. Alternatively (or additionally), the EM tracking system may store the specific model to a server accessible over a network on which the EM tracking system communicates such that the specific model is associated an identifier (e.g., an RFID) reported by the tool. This storage (in whatever case) may allow subsequent uses of the optimized characteristics for the distorter and/or the tool including the distorter in the EM tracking system without having to repeat the optimization process. It may also allow the specific model for the distorter and/or the tool including the distorter to be continuously improved through repeated optimization starting from the previous version of the specific model, corresponding with repetitious use of the distorter and/or the tool including the distorter as described above.

Once any such optimized characteristics (e.g., in geometry, magnetic permeability, electrical conductivity, etc.) are determined, these values may be used to determine, for example, an optimized (more accurate) pose (e.g., position and/or orientation) of the distorter and/or the tool including the distorter. They may also and/or alternatively be used to determine an optimized distorter magnetic moment $M_o$ (e.g., by substituting in the optimized characteristics in the formula(s) for $M_i$ described above) for the distorter. Then the optimized distortion field $D_o$ can be determined with $D_o(M_o, r)$ in the manner described above (e.g., by substituting $M_o$ and an optimized r into a formula for $D_i(M_i, r)$ as described above.

Accordingly, $D_o$ may be said to be an approximation of the distortion field caused by the distorter that has been optimized from $D_i$, and that such optimization may be based (at least in part) on data representing one or more experienced EM fields as distorted by a second distortion field caused by the distorter as reported by one or more EM trackers.

Such optimizations may occur on a per EM sensor basis within a single EM tracker. An EM tracker may have multiple EM sensors (such as multiple induction coils). Optimizations for these sensors may correct signal magnitudes and signal phases relative to an approximated distortion. For example, each sensor may experience a component magnitude and phase of each of a transmitted EM field and a distortion field. An initial distortion field model may imply a different component magnitude and phase than what actually occurs. The distortion field model may be adjusted appropriately. As an example, a sensor may experience a component magnitude of 1 mV and a relative phase of 84 degrees. An initial distortion field model may imply a component magnitude of 1 mV and a relative phase of 85 degrees. With this difference, a distorter resistance may be optimized.

Such optimizations may occur on a per EM tracker basis. For example, optimizations driven by one or more individual EM trackers may correct for tracking metrics relative to an approximated distortion.

Such optimizations may occur across multiple EM trackers. For example, optimizations driven by a set of multiple EM trackers may correct for tracking metrics, relative poses, positions, orientations, and magnitudes of an approximated distortion.

Such optimizations may be checked against one or more constraints for the position, orientation, magnitude, and or phase of the optimized distortion field. For example, each of the position, orientation, magnitude, and/or phase of the optimized distortion field generated using optimized characteristics may be checked against an initial distortion field using the characteristics from the general model for the distorter/tool including the distorter in order to ensure that the differences between these two distortion fields are within certain permissible or expected bounds. For example, it may occur that an optimization process may attempt to move a dipole position outside the geometry of the distorter. This would indicate that some error has occurred, and such an optimization would not be performed.

Based on the optimizations as tempered by the constraints, corrections are made to the general model for the distorter/tool including the distorter to generate the specific model for the distorter/tool including the distorter, which is used to generate the corresponding optimized distortion field. The specific model for the distorter/tool including the distorter may be saved in a memory of the EM tracking system.

Figure 6:
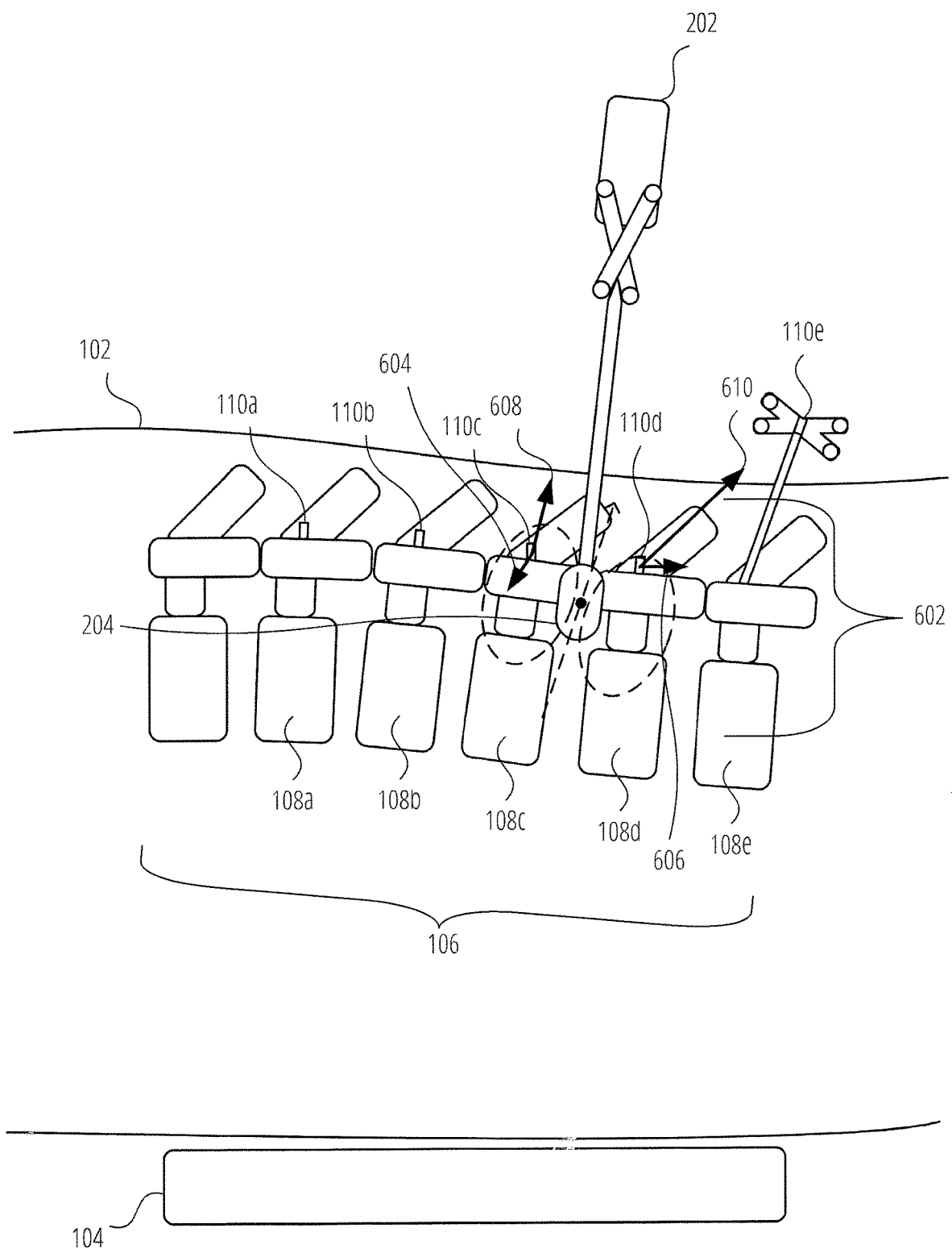
FIG. 6 illustrates the disposition of a tool near a spinal column of the patient incident to the performance of a surgical procedure, with an optimized distortion field superimposed over a tip of the tool, according to an embodiment.

FIG. 6 illustrates the disposition of the tool 202 near the spinal column 106 of the patient 102 incident to the performance of a surgical procedure, with an optimized distortion field 602 superimposed over the tip 204 of the tool 202, according to an embodiment. The optimized distortion field 602 may conceptually represent $D_o$ (when using a dipole model). As can be seen by comparison to FIG. 5, the optimized distortion field 602 is slightly different (e.g., is different in one or more of position, orientation, magnitude, and/or phase) than the initial distortion field 502 due to the optimization process described herein.

As illustrated, the EM tracker 110c and the EM tracker 110d are near the initial optimized distortion field 602. Accordingly, the EM tracking system presumes some non-zero distortive effect due to the interaction of the EM field transmitted by the EM emitter 104 and the tip 204 on these EM trackers. A first distortion vector 604 and a second distortion vector 606 (representing the presumed effect of the distortion field as represented by the optimized distortion field 602 at, respectively, the positions of the EM tracker 110c and the EM tracker 110d) may be calculated by the EM tracking system using $D_o(M_o, r)$ in the manner described herein.

The EM tracker 110c reports to the EM tracking system the first experienced EM field 608. The first experienced EM field 608 is a raw reading taken by the EM tracker 110c that has not been corrected for the effects of the distortion field represented by the first distortion vector 604. The EM tracker 110d reports to the EM tracking system the second experienced EM field 610. The second experienced EM field 610 is a raw reading taken by the EM tracker 110d that has not been corrected for the effects of the distortion field represented by the second distortion vector 606.

Figure 7:
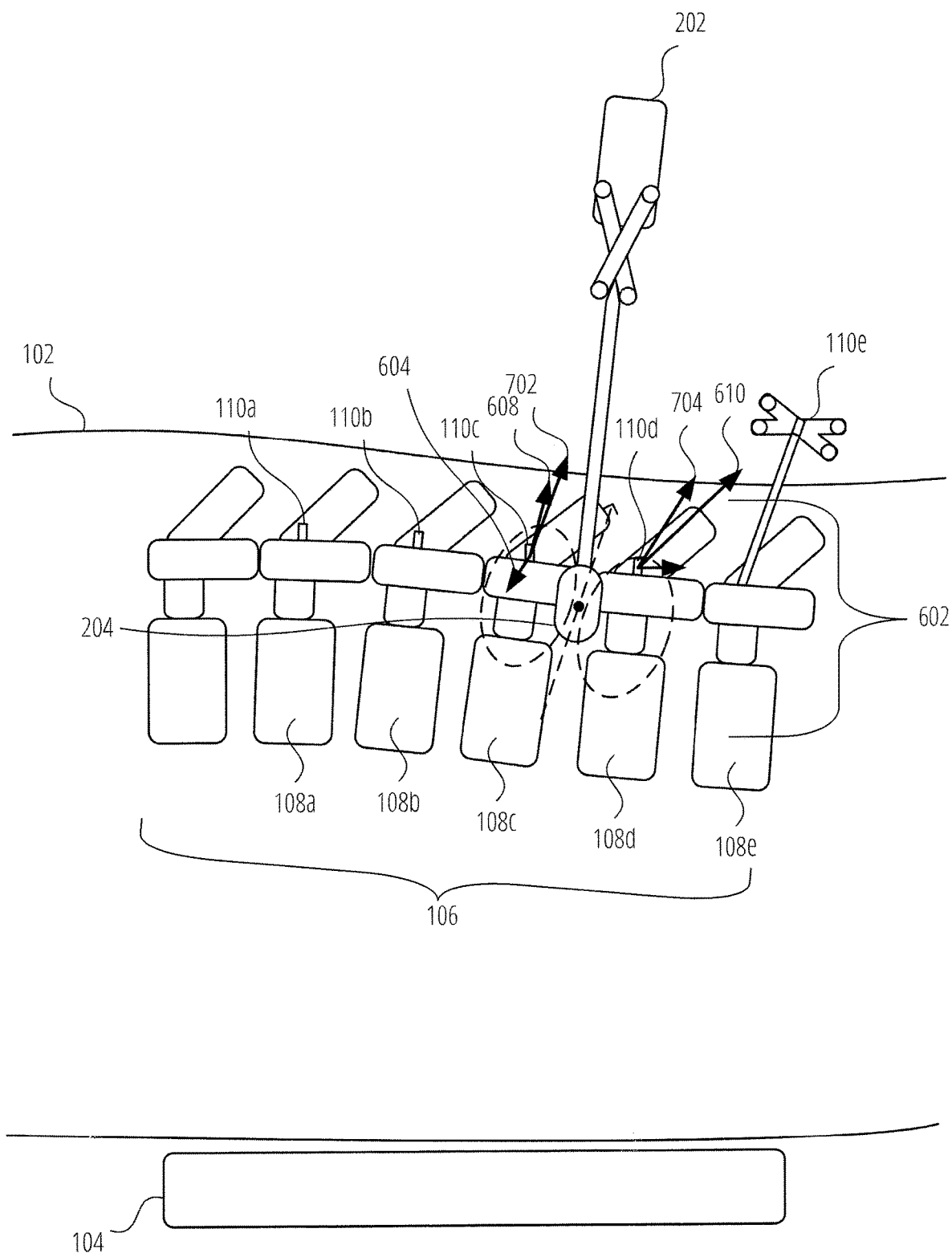
FIG. 7 illustrates the disposition of a tool near a spinal column of a patient incident to the performance of a surgical procedure, with an optimized distortion field superimposed over a tip of the tool being used to calculate data representing a first corrected experienced EM field and a second corrected experienced EM field, according to an embodiment.

FIG. 7 illustrates the disposition of the tool 202 near the spinal column 106 of the patient 102 incident to the performance of a surgical procedure, with an optimized distortion field 602 superimposed over the tip 204 of the tool 202 being used to calculate data representing a first corrected experienced EM field 702 and a second corrected experienced EM field 704, according to an embodiment. The first corrected experienced EM field 702 may be calculated by the system by taking the first experienced EM field 608 reported by the EM tracker 110c and correcting it for the first distortion vector 604. The second corrected experienced EM field 704 may be calculated by the system by taking the second experienced EM field 610 reported by the EM tracker 110d and correcting it for the second distortion vector 606.

The system then uses the first corrected experienced EM field 702 and/or the second corrected experienced EM field 704 in tracking operations that use the experienced EM fields of the EM tracker 110c and/or the EM tracker 110d to determine, for example, the pose(s) of one or more of the vertebrae 108a-108e, as appropriate.

While FIG. 7 has illustrated the calculation of the first corrected experienced EM field 702 and the first corrected experienced EM field 702 using the optimized distortion field 602, it is contemplated that in some systems that do not optimize their distortion fields may instead use, for example, an approximation analogous to the initial distortion field 502 to analogously calculate one or more corrected experienced EM fields.

Figure 8:
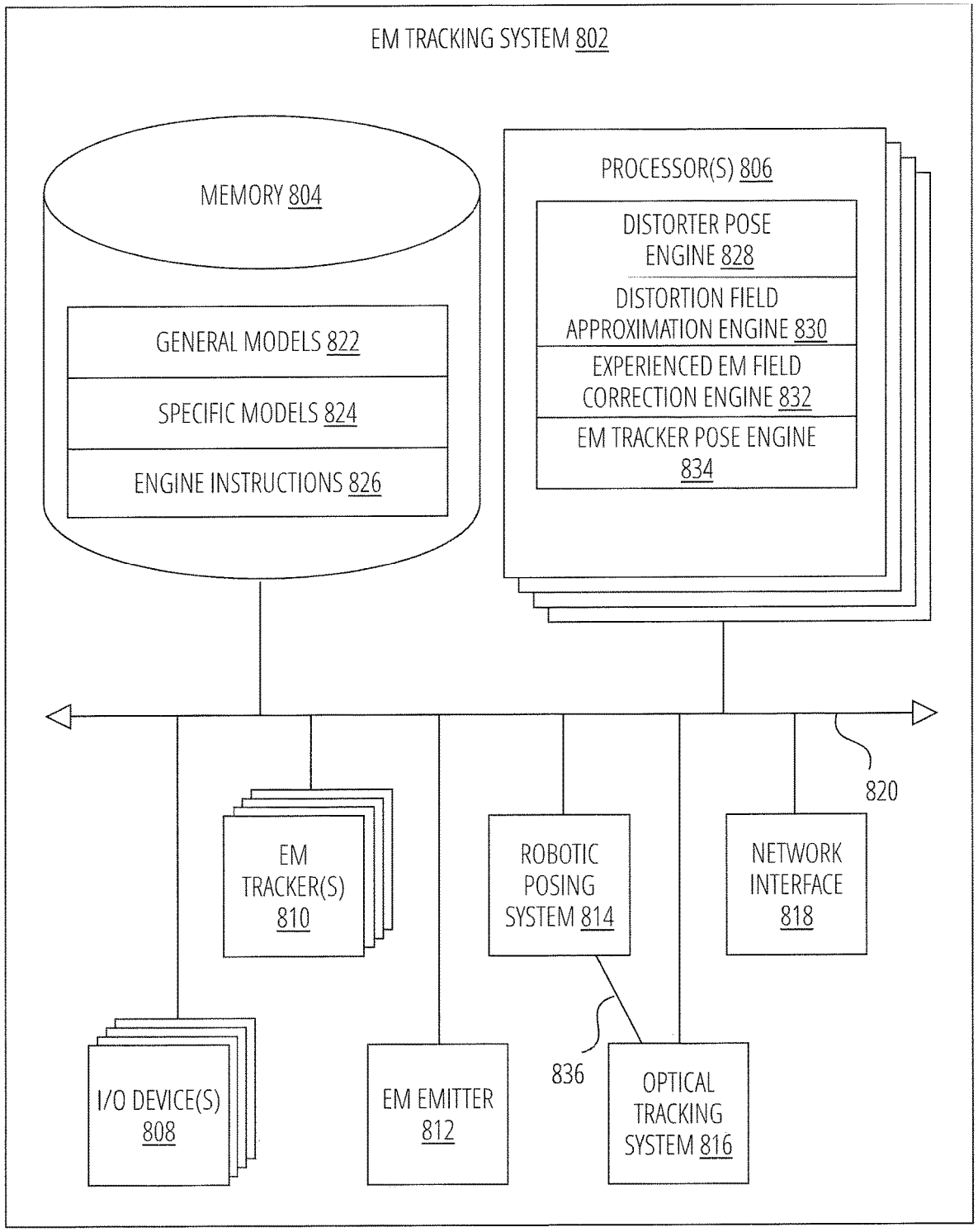
FIG. 8 illustrates the components of an EM tracking system according to some embodiments.

FIG. 8 illustrates the components of an EM tracking system 802 according to some embodiments. The EM tracking system 802 includes a memory 804, one or more processor(s) 806, one or more I/O device(s) 808, one or more EM tracker(s) 810, an EM emitter 812, a robotic posing system 814, an optical tracking system 816, and a network interface 818. Each of these elements may be electronically coupled by a communication interface 820, which may represent one or more internal communications interfaces (such as one or more traditional data busses between, e.g., the memory 804, the processor(s) 806, and the network interface 818) and/or one or more external communications interfaces (such as external data wiring to, e.g., I/O device(s) 808, EM tracker(s) 810, the robotic posing system 814, and/or the optical tracking system 816). Other arrangements are contemplated. It is also contemplated that some EM tracking systems may also include and or use a lidar tracking system and/or visible light tracking system (among other possible tracking systems), as described above.

The memory 804 includes one or more general models 822, one or more specific models 824, and the engine instructions 826 that may be executed by the processor(s) 806.

The processor(s) 806 may operate computer-readable instructions found at the memory 804 of the EM tracking system 802 to perform the various functions thereof as engines. For example, the processor(s) 806 may operate (execute) the distorter pose engine 828, the distortion field approximation engine 830, the experienced EM field correction engine 832, and the EM tracker pose engine 834. These instructions may be executed as found in, for example, the memory 804 of the EM tracking system 802 (e.g., the engine instructions 826).

The I/O device(s) 808 may provide a way for a local user to provide input/receive output from the system. Examples of such I/O device(s) 808 may include a keyboard, a mouse, a monitor, a speaker, etc. Any results determined by the EM tracking system 802 as described herein (e.g., positions of anatomical structures, corrected experienced EM fields, etc.) may be communicated to a user of the EM tracking system 802 via the one or more I/O device(s) 808.

The EM tracker(s) 810 may be connected to an anatomical structure of a patient and may each report a respective experienced EM field to the EM tracking system 802 generally, in the manner described above. Each of the EM tracker(s) 810 may be connected via, for example, a wire that carries such signaling from the EM tracker(s) 810 to, for example, the processor(s) 806 of the EM tracking system 802.

The EM emitter 812 may be disposed near the patient such that one or more EM fields transmitted by the EM emitter 812 will effectively cover the one or more EM tracker(s) 810 within an area of interest of the patient, as described above.

The robotic posing system 814 may be responsible for establishing a pose (e.g., a position and orientation) of, for example, distorters and/or tools including distorters within the EM field transmitted by the EM emitter 812. As described above, the robotic posing system 814 may report to the EM tracking system 802 generally its own configuration, allowing the EM tracking system 802 to determine the position and/or orientation of the distorter and/or tool including the distorter that is being manipulated within the EM field by the robotic posing system 814.

The optical tracking system 816 may optically track a distorter and/or a tool including the distorter within an EM field. The optical tracking system 816 may accordingly be able to report to the EM tracking system 802 generally regarding the position and/or orientation of the distorter and/or tool including the distorter.

It is anticipated that in some embodiments, the robotic posing system 814 and the optical tracking system 816 may be co-registered 836 such that data from both can be used generally in EM tracking system 802 to determine a posing (e.g., a position and/or an orientation) of a distorter within the EM field. As described above, either or both of these may be further co-registered to a spatial volume for EM tracking used by the EM tracking system 802.

The network interface 818 may transport data into and out of the EM tracking system 802. For example, any results determined by the EM tracking system 802 as described herein (e.g., positions of anatomical structures, corrected experienced EM fields, etc.) may be transported to another device via the network interface 818. Further, it is anticipated that in some embodiments, the robotic posing system 814 and the optical tracking system 816 may not directly be elements of the EM tracking system 802 as illustrated in FIG. 8, but rather may be separate entities that communicate with the EM tracking system 802 via the network interface 818. In this case, the EM tracking system 802 may communicate with and use either/both of the robotic posing system 814 and/or the optical tracking system 816 via the network interface 818, analogously as described herein.

The general models 822 may include one or more models for one or more distorters and/or tools including such distorters. These general models 822 may include (record) characteristics (e.g., geometry, magnetic permeability, electrical conductivity, etc.) regarding these distorters and/or the tools including the distorters. These general models 822 may be based on what is pre-presumed (e.g., a pre-programmed parameterization) about the distorters and/or the tools including the distorters. It may alternatively be that this general model is based on prior experience by the EM tracking system 802 with one or more of the distorters and/or tools including the distorters.

The specific models 824 may include one or more models for one or more distorters and/or tools including the distorter. These specific models 824 may include (record) characteristics (e.g., geometry, magnetic permeability, electrical conductivity, etc.) regarding these distorters and/or the tools including the distorters. As described above, such specific models 824 may include models for specific instances of distorters and/or tools including the distorters made by the application of a general model corresponding to a distorter and/or tool including the distorter together with differences between the distorter and/or its tool from the general model as determined while the distorter and/or its tool are in use (such as, for example, differences in EM response and/or geometry).

The engine instructions 826 may include instructions for one or more engines, including the distorter pose engine 828, the distortion field approximation engine 830, the experienced EM field correction engine 832, and the EM tracker pose engine 834. Various ones of these engines may be active within the EM tracking system 802 at different times, as the processor(s) 806 operate the relevant instructions thereof by using the engine instructions 826.

The distorter pose engine 828 may perform functionalities as described herein for determining a pose of a distorter within an EM field transmitted by the EM emitter 812. For example, the distorter pose engine 828 may operate/interface with the robotic posing system 814 and/or the optical tracking system 816 (and/or another tracking system) for the purposes of making distorter pose determinations. Further, the distorter pose engine 828 may make pose determinations using an EM tracker of, for example, a tool comprising the distorter, in the manner described herein.

The distortion field approximation engine 830 may perform functionalities described herein for approximating a distortion field (e.g., calculating either or both of $D_i$ and/or $D_o$).

The experienced EM field correction engine 832 may perform functionalities described herein for generating one or more distortion vectors according to $D_i$ and/or $D_o$. Further, the experienced EM field correction engine 832 may perform the correction on one or more experienced EM fields from the EM tracker(s) 810 using said distortion vectors, as described herein.

The EM tracker pose engine 834 may perform functionalities described herein for using the corrected experienced EM fields to locate one or more anatomical structures to which the EM tracker(s) 810 are attached within the area of interest of the patient.

Figure 9:
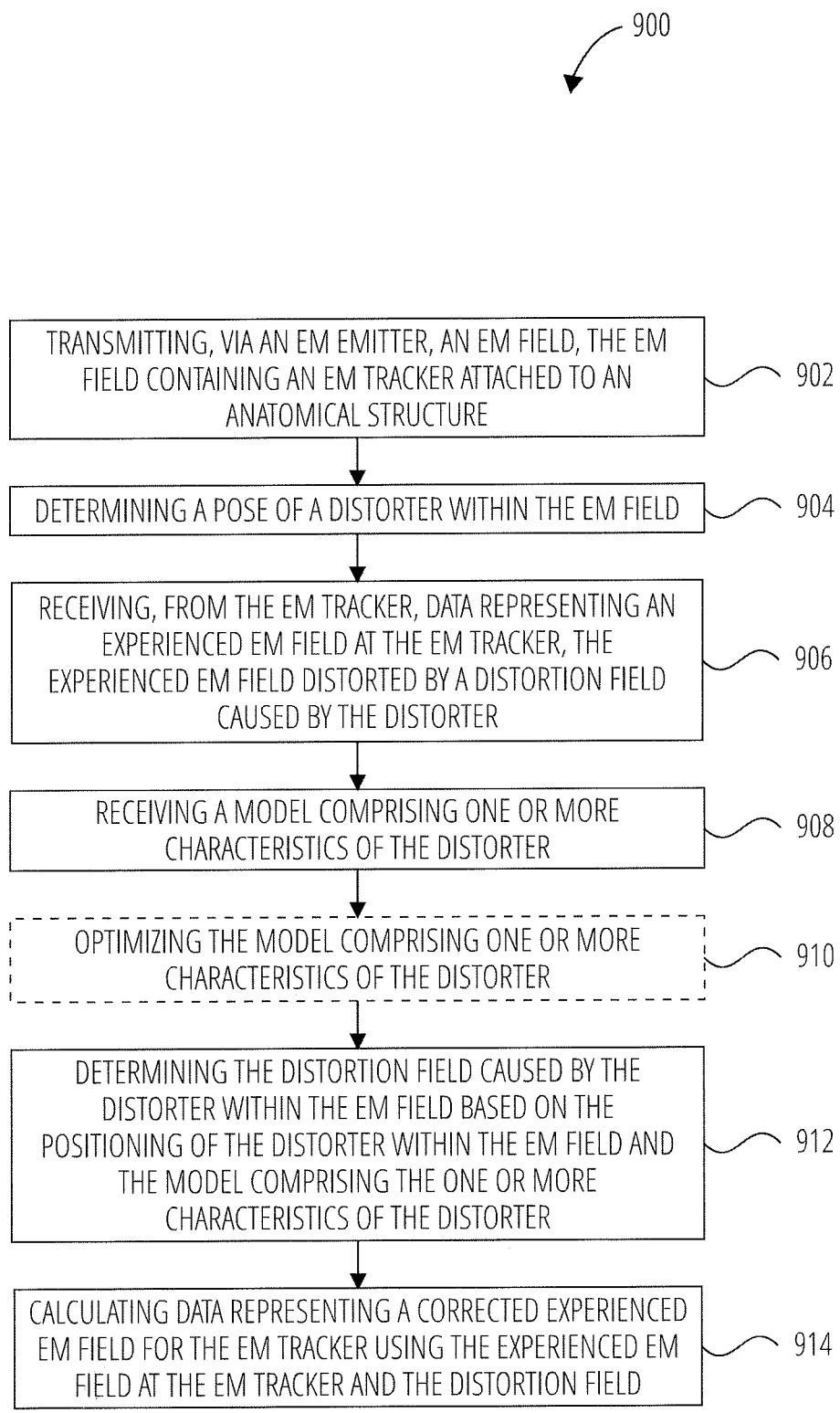
FIG. 9 illustrates a method of an EM tracking system, according to an embodiment.

FIG. 9 illustrates a method 900 of an EM tracking system, according to an embodiment. The method 900 includes transmitting 902, via an EM emitter, an EM field, the EM field containing an EM tracker attached to an anatomical structure.

The method 900 further includes determining 904 a pose of a distorter within the EM field.

The method 900 further includes receiving 906, from the EM tracker, data representing an experienced EM field at the EM tracker, the experienced EM field distorted by a distortion field caused by the distorter.

The method 900 further includes receiving 908 a model comprising one or more characteristics of the distorter.

The method 900 further optionally includes optimizing 910 the model comprising one or more characteristics of the distorter. Optimization may be based on data representing currently and previously reported experienced EM field that included the distorter.

The method 900 further includes determining 912 the distortion field caused by the distorter within the EM field based on the pose of the distorter within the EM field and the model comprising the one or more characteristics of the distorter.

The method 900 further includes calculating 914 data representing a corrected experienced EM field for the EM tracker using the experienced EM field at the EM tracker and the distortion field.

While the description of FIGS. 1-9 has used an EM emitter and multiple EM trackers, it is contemplated that analogous principles could be applied in the case of EM trackers that provide EM fields to others of the EM trackers. It is also contemplated that analogous principles could be applied in the case of EM trackers that provide EM fields to an EM receiver.

Further, while the description of FIGS. 2-7 describes the use of a tool 202 comprising a single distorter (the tip 204), it is contemplated that some tools may comprise multiple distorters. In these cases, the multiple disorders may each be individually tracked, modeled and accounted for, as described above. In these cases, multiple distortion vectors (one for each distorter in the tool) may be generated relative to an EM tracker, and may together be summed with the EM tracker's experienced EM field in order to generate a corrected experienced EM field for the EM tracker.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

For one or more embodiments, at least one of the components set forth in one or more of the preceding figures may be configured to perform one or more operations, techniques, processes, and/or methods as set forth in the Example Section below.

Example Section

The following Examples pertain to further embodiments.

Example 1 may include a method comprising: determining a pose of a distorter within an electromagnetic (EM) field; receiving, from an EM tracker in the EM field, data representing an experienced EM field at the EM tracker, the experienced EM field being distorted by a distortion field caused by the distorter within the EM field; determining the distortion field caused by the distorter within the EM field based on the determined pose of the distorter within the EM field and a model of the distorter comprising one or more characteristics of the distorter; and calculating a corrected experienced EM field for the EM tracker using the experienced EM field at the EM tracker and the determined distortion field.

Example 2 may include the method of Example 1, further comprising optimizing the model of the distorter based on the data representing the experienced EM field.

Example 3 may include the method of Example 1, wherein the distortion caused by the distorter within the EM field is a first distortion field and wherein the experienced EM field is a first experienced EM field, the method further comprising optimizing the model of the distorter based on data representing a second experienced EM field impacted by a second distortion field caused by the distorter.

Example 4 may include the method of Example 1, wherein the distortion field is modeled as one of a dipole, a multiple dipole, a multipole, an effective charge, an effective current, a boundary element method model, a finite element analysis model, and a measurement-based model.

Example 5 may include the method of Example 1, wherein the pose of the distorter includes one or more of a position of the distorter within the EM field and an orientation of the distorter relative to one of the EM emitter and the EM tracker.

Example 6 may include the method of Example 1, wherein determining the distortion field caused by the distorter comprises determining one or more of a location, an orientation, a magnitude, and a phase of the distortion field.

Example 7 may include the method of Example 1, wherein the model of the distorter comprises a relative magnetic permeability of the distorter.

Example 8 may include the method of Example 1, wherein the model of the distorter comprises an electrical conductivity of the distorter.

Example 9 may include the method of Example 1, wherein the model of the distorter comprises a physical dimension of the distorter.

Example 10 may include the method of Example 1, wherein the pose of the distorter is determined using configuration tracking by a robotic posing system.

Example 11 may include the method of Example 1, wherein the pose of the distorter is determined using optical tracking by an optical tracking system.

Example 12 may include the method of Example 1, wherein the pose of the distorter is determined using configuration tracking by a robotic posing system and optical tracking by an optical tracking system.

Example 13 may include the method of Example 1, wherein the pose of the distorter is determined using an EM tracker of a tool comprising the distorter.

Example 14 may include the method of Example 1, wherein the pose of the distorter is determined using data from an EM tracker of a tool comprising the distorter and data from an optical tracking system.

Example 15 may include a computing apparatus comprising: a processor; and a memory storing instructions that, when executed by the processor, configure the apparatus to: determine a pose of a distorter within an electromagnetic (EM) field; receive, from an EM tracker in the EM field, data representing an experienced EM field at the EM tracker, the experienced EM field being distorted by a distortion field caused by the distorter within the EM field; determine the distortion field caused by the distorter within the EM field based on the determined pose of the distorter within the EM field and a model of the distorter comprising one or more characteristics of the distorter; and calculate a corrected experienced EM field for the EM tracker using the experienced EM field at the EM tracker and the determined distortion field.

Example 16 may include the computing apparatus of Example 15, wherein the instructions, when executed by the processor, further configure the apparatus to optimize the model of the distorter based on the data representing the experienced EM field.

Example 17 may include the computing apparatus of Example 15, wherein the distortion caused by the distorter within the EM field is a first distortion field and wherein the experienced EM field is a first experienced EM field, and wherein the instructions, when executed by the processor, further configure the apparatus to optimize the model of the distorter based on data representing a second experienced EM field impacted by a second distortion field caused by the distorter.

Example 18 may include the computing apparatus of Example 15, wherein the distortion field is modeled as one of a dipole, a multiple dipole, a multipole, an effective charge, an effective current, a boundary element method model, a finite element analysis model, and a measurement-based model.

Example 19 may include the computing apparatus of Example 15, wherein the pose of the distorter includes one or more of a position of the distorter within the EM field and an orientation of the distorter relative to one of the EM emitter and the EM tracker.

Example 20 may include the computing apparatus of Example 15, wherein the instructions, when executed by the processor, configure the apparatus to determine the distortion field caused by the distorter by determining one or more of a location, an orientation, a magnitude, and a phase of the distortion field.

Example 21 may include the computing apparatus of Example 15, wherein the instructions, when executed by the processor, configure the apparatus to determine the distortion field based on a relative magnetic permeability of the distorter that is recorded in the model of the distorter.

Example 22 may include the computing apparatus of Example 15, wherein the instructions, when executed by the processor, configure the apparatus to determine the distortion field based on an electrical conductivity of the distorter that is recorded in the model of the distorter.

Example 23 may include the computing apparatus of Example 15, wherein the instructions, when executed by the processor, configure the apparatus to determine the distortion field based on a physical dimension of the distorter that is recorded in the model of the distorter.

Example 24 may include the computing apparatus of Example 15, wherein the instructions, when executed by the processor, configure the apparatus to determine the pose of the distorter using configuration tracking at a robotic posing system.

Example 25 may include the computing apparatus of Example 15, wherein the instructions, when executed by the processor, configure the apparatus to determine the pose of the distorter using optical tracking by an optical tracking system.

Example 26 may include the computing apparatus of Example 15, wherein the instructions, when executed by the processor, configure the apparatus to determine the pose of the distorter using configuration tracking at a robotic posing system and optical tracking by an optical tracking system.

Example 27 may include the computing apparatus of Example 15, wherein the instructions, when executed by the processor, configure the apparatus to determine the pose of the distorter using an EM tracker of a tool comprising the distorter.

Example 28 may include the computing apparatus of Example 15, wherein the instructions, when executed by the processor, configure the apparatus to determine the pose of the distorter using data from an EM tracker of a tool comprising the distorter and data from an optical tracking system.

Example 29 may include an electromagnetic (EM) tracking system, comprising: one or more EM trackers; an EM emitter configured to transmit an EM field containing the one or more EM trackers; an optical tracking system configured to track the distorter using optical tracking; a memory comprising a model of the distorter comprising one or more characteristics of the distorter; and one or more processors in electronic communication with the one or more EM trackers, the EM emitter, the optical tracking system, and the memory, the one or more processors configured to: determine a pose of the distorter within the EM field; receive, from each of the one or more EM trackers in the EM field, data representing an experienced EM field at each of the one or more EM trackers, each experienced EM field being distorted by a distortion field caused by the distorter within the EM field; determine the distortion field caused by the distorter within the EM field based on the determined pose of the distorter within the EM field and the model of the distorter; and calculate a corrected experienced EM field for each of the one or more EM trackers using the experienced EM field at each of the one or more EM trackers and the determined distortion field.

Example 30 may include the EM tracking system of Example 29, wherein the one or more processors are further configured to optimize the model of the distorter based on the data representing the experienced EM field.

Example 31 may include the EM tracking system of Example 29, wherein the distortion field caused by the distorter within the EM field is a first distortion field, wherein the one or more processors are further configured to optimize the model comprising the one or more characteristics of the distorter based on data representing an experienced EM field as distorted by a second distortion field caused by the distorter.

Example 32 may include the EM tracking system of Example 29, wherein the distortion field is modeled as one of a dipole, a multiple dipole, a multipole, an effective charge, an effective current, a boundary element method model, a finite element analysis model, and a measurement-based model.

Example 33 may include the EM tracking system of Example 29, wherein the pose of the distorter includes one or more of a position of the distorter within the EM field and an orientation of the distorter relative to one of the EM emitter and the one or more EM trackers.

Example 34 may include the EM tracking system of Example 29, wherein the one or more processors are further configured to determine the distortion field caused by the distorter by determining one or more of a location, an orientation, a magnitude, and a phase of the distortion field.

Example 35 may include the EM tracking system of Example 29, wherein the one or more processors are further configured to determine the distortion field based on a magnetic permeability of the distorter that is recorded in the model of the distorter.

Example 36 may include the EM tracking system of Example 29, wherein the one or more processors are further configured to determine the distortion field based on an electrical conductivity of the distorter that is recorded in the model of the distorter.

Example 37 may include the EM tracking system of Example 29, wherein the one or more processors are further configured to determine the distortion field based on a physical dimension of the distorter that is recorded in the model of the distorter.

Example 38 may include the EM tracking system of Example 29, wherein the one or more processors is further in communication with a robotic posing system, and where the one or more processors are further configured to determine the pose of the distorter using configuration tracking data from the robotic posing system.

Example 39 may include the EM tracking system of Example 29, wherein the one or more processors are further configured to determine the pose of the distorter using optical tracking data from the optical tracking system.

Example 40 may include the EM tracking system of Example 29, wherein the one or more processors are further configured to determine the pose of the distorter using configuration tracking data from the robotic posing system and optical tracking data from the optical tracking system.

Example 41 may include the EM tracking system of Example 29, wherein the one or more processors are further configured to determine the pose of the distorter using an EM tracker of a tool comprising the distorter.

Example 42 may include the EM tracking system of Example 29, wherein the one or more processors are further configured to determine the pose of the distorter using data from an EM tracker of a tool comprising the distorter and data from the optical tracking system.

Example 43 may include an apparatus comprising means to perform one or more elements of a method described in or related to any of the above Examples, or any other method or process described herein.

Example 44 may include one or more non-transitory computer-readable media comprising instructions to cause an electronic device, upon execution of the instructions by one or more processors of the electronic device, to perform one or more elements of a method described in or related to any of the above Examples, or any other method or process described herein.

Example 45 may include an apparatus comprising logic, modules, or circuitry to perform one or more elements of a method described in or related to any of the above Examples, or any other method or process described herein.

Example 46 may include a method, technique, or process as described in or related to any of the above Examples, or portions or parts thereof.

Example 47 may include an apparatus comprising: one or more processors and one or more computer-readable media comprising instructions that, when executed by the one or more processors, cause the one or more processors to perform the method, techniques, or process as described in or related to any of the above Examples, or portions thereof.

Example 48 may include a signal as described in or related to any of the above Examples, or portions or parts thereof.

Example 49 may include a datagram, packet, frame, segment, protocol data unit (PDU), or message as described in or related to any of the above Examples, or portions or parts thereof, or otherwise described in the present disclosure.

Example 50 may include a signal encoded with data as described in or related to any of the above Examples, or portions or parts thereof, or otherwise described in the present disclosure.

Example 51 may include a signal encoded with a datagram, packet, frame, segment, PDU, or message as described in or related to any of the above Examples, or portions or parts thereof, or otherwise described in the present disclosure.

Example 52 may include an electromagnetic signal carrying computer-readable instructions, wherein execution of the computer-readable instructions by one or more processors is to cause the one or more processors to perform the method, techniques, or process as described in or related to any of the above Examples, or portions thereof.

Example 53 may include a computer program comprising instructions, wherein execution of the program by a processing element is to cause the processing element to carry out the method, techniques, or process as described in or related to any of the above Examples, or portions thereof.

Example 54 may include a signal in a wireless network as shown and described herein.

Example 55 may include a method of communicating in a wireless network as shown and described herein.

Example 56 may include a system for providing wireless communication as shown and described herein.

Example 57 may include a device for providing wireless communication as shown and described herein.

Any of the above described Examples may be combined with any other Example (or combination of Examples), unless explicitly stated otherwise. The foregoing description of one or more implementations provides illustration and description, but is not intended to be exhaustive or to limit the scope of embodiments to the precise form disclosed. Modifications and variations are possible in light of the above teachings or may be acquired from practice of various embodiments.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. Accordingly, the present embodiments are to be considered illustrative and not restrictive, and the description is not to be limited to the details given herein, but may be modified within the scope and equivalents of the appended claims.

The invention claimed is:

1. A method comprising:
   determining a pose of a distorter within an electromagnetic (EM) field;
   receiving, from an EM tracker in the EM field, data representing an experienced EM field at the EM tracker, the experienced EM field being distorted by a distortion field caused by the distorter within the EM field;
   determining the distortion field caused by the distorter within the EM field based on the determined pose of the distorter within the EM field and a model of the distorter comprising one or more characteristics of the distorter; and
   calculating a corrected experienced EM field for the EM tracker using the experienced EM field at the EM tracker and the determined distortion field.

2. The method of claim 1, further comprising optimizing the model of the distorter based on the data representing the experienced EM field.

3. The method of claim 1, wherein the distortion caused by the distorter within the EM field is a first distortion field and wherein the experienced EM field is a first experienced EM field, the method further comprising optimizing the model of the distorter based on data representing a second experienced EM field impacted by a second distortion field caused by the distorter.

4. The method of claim 1, wherein the distortion field is modeled as one of a dipole, a multiple dipole, a multipole, an effective charge, an effective current, a boundary element method model, a finite element analysis model, and a measurement-based model.

5. The method of claim 1, wherein the pose of the distorter includes one or more of a position of the distorter within the EM field and an orientation of the distorter relative to one of the EM emitter and the EM tracker.

6. The method of claim 1, wherein determining the distortion field caused by the distorter comprises determining one or more of a location, an orientation, a magnitude, and a phase of the distortion field.

7. The method of claim 1, wherein the model of the distorter comprises a relative magnetic permeability of the distorter.

8. The method of claim 1, further comprising determining the pose of the distorter using data from an EM tracker of a tool comprising the distorter and data from the optical tracking system.

9. A computing apparatus comprising:
a processor; and
a memory storing instructions that, when executed by the processor, configure the apparatus to:
determine a pose of a distorter within an electromagnetic (EM) field;
receive, from an EM tracker in the EM field, data representing an experienced EM field at the EM tracker, the experienced EM field being distorted by a distortion field caused by the distorter within the EM field;
determine the distortion field caused by the distorter within the EM field based on the determined pose of the distorter within the EM field and a model of the distorter comprising one or more characteristics of the distorter; and
calculate a corrected experienced EM field for the EM tracker using the experienced EM field at the EM tracker and the determined distortion field.

10. The computing apparatus of claim 9, wherein the instructions, when executed by the processor, configure the apparatus to determine the distortion field based on a physical dimension of the distorter that is recorded in the model of the distorter.

11. The computing apparatus of claim 9, wherein the instructions, when executed by the processor, configure the apparatus to determine the pose of the distorter using configuration tracking at a robotic posing system.

12. The computing apparatus of claim 9, wherein the instructions, when executed by the processor, configure the apparatus to determine the pose of the distorter using optical tracking by an optical tracking system.

13. The computing apparatus of claim 9, wherein the instructions, when executed by the processor, configure the apparatus to determine the pose of the distorter using configuration tracking at a robotic posing system and optical tracking by an optical tracking system.

14. The computing apparatus of claim 9, wherein the distortion field is modeled as one of a dipole, a multiple dipole, a multipole, an effective charge, an effective current, a boundary element method model, a finite element analysis model, and a measurement-based model.

15. The computing apparatus of claim 9, wherein the instructions, when executed by the processor, configure the apparatus to determine the pose of the distorter using data from an EM tracker of a tool comprising the distorter and data from the optical tracking system.

16. An electromagnetic (EM) tracking system, comprising:
one or more EM trackers;
an EM emitter configured to transmit an EM field containing the one or more EM trackers;
an optical tracking system configured to track the distorter using optical tracking;
a memory comprising a model of the distorter comprising one or more characteristics of the distorter; and
one or more processors in electronic communication with the one or more EM trackers, the EM emitter, the optical tracking system, and the memory, the one or more processors configured to:
determine a pose of the distorter within the EM field;
receive, from each of the one or more EM trackers in the EM field, data representing an experienced EM field at each of the one or more EM trackers, each experienced EM field being distorted by a distortion field caused by the distorter within the EM field;
determine the distortion field caused by the distorter within the EM field based on the determined pose of the distorter within the EM field and the model of the distorter; and
calculate a corrected experienced EM field for each of the one or more EM trackers using the experienced EM field at each of the one or more EM trackers and the determined distortion field.

17. The EM tracking system of claim 16, wherein the distortion field is modeled as one of a dipole, a multiple dipole, a multipole, an effective charge, an effective current, a boundary element method model, a finite element analysis model, and a measurement-based model.

18. The EM tracking system of claim 16, wherein the one or more processors are further configured to determine the distortion field based on an electrical conductivity of the distorter that is recorded in the model of the distorter.

19. The EM tracking system of claim 16, wherein the one or more processors are further configured to determine the pose of the distorter using configuration tracking data from the robotic posing system and optical tracking data from the optical tracking system.

20. The EM tracking system of claim 16, wherein the one or more processors are further configured to determine the pose of the distorter using an EM tracker of a tool comprising the distorter.

21. The EM tracking system of claim 16, wherein the one or more processors are further configured to determine the pose of the distorter using data from an EM tracker of a tool comprising the distorter and data from the optical tracking system.

* * * * *